United States Patent [19]

Lidert et al.

[11] Patent Number: 5,344,958
[45] Date of Patent: Sep. 6, 1994

[54] INSECTICIDAL N'-SUBSTITUTED-N,N'-DIACYLHYDRAZINES

[75] Inventors: Zev Lidert, Doylestown; Dat P. Le, North Wales, both of Pa.

[73] Assignee: Rohm and Haas Company, Philadelphia, Pa.

[21] Appl. No.: 984,189

[22] Filed: Nov. 23, 1992

[51] Int. Cl.$^5$ .................... C07C 69/78; C07C 65/21
[52] U.S. Cl. ........................... 560/64; 560/65; 562/473; 562/474
[58] Field of Search ............... 560/61, 64, 65, 129, 560/226; 562/473

[56] References Cited

U.S. PATENT DOCUMENTS

| | | | |
|---|---|---|---|
| 4,389,401 | 6/1983 | Smolanoff | 424/248.56 |
| 4,954,655 | 9/1990 | Kelly | 564/464 |
| 4,985,461 | 1/1991 | Hsu et al. | 514/615 |
| 5,110,979 | 5/1992 | Nguyen | 560/61 |
| 5,110,986 | 5/1992 | Kelly | 564/149 |
| 5,117,057 | 5/1992 | Hsu et al. | 564/149 |

FOREIGN PATENT DOCUMENTS

496342 7/1992 European Pat. Off. .

OTHER PUBLICATIONS

Meyers, et al., pp. 3881–3886, 1961, "Chemistry of Aryloxazolines", J. Org. Chem. vol. 46.
Fringuelli, et al., pp. 4249–4256, 1969 "Synthesis of Methyl(±)-7-oxo-8-methyl-podocarp-8-en-16-oate", Tetrahedron vol. 25.
Cresp et al., pp. 2435–2447, 1974 "Synthesis of Piloquinone . . . " J. Chem. Soc. Perkin Trans. I, vol. 21.
McAlees, pp. 2030–2036, 1977, "Hydrogenation of Substituted Phthalic Anhydrides . . . " J. Chem. Soc. Perkin Trans I.
Meyers, et al., pp. 7383–7385, 1975, "Oxazolines XXIII . . . " J. Amer. Chem. Soc, 97:25.
Meyers, et al., pp. 1372–1379, 1977, "Nucleophilic Aromatic Substitution . . . ", J. Org. Chem, vol. 43, No. 7.
Campbell, pp. 3963–3966, 1986, "Metallation of Rigid 2-Aryl-1,3-Dioxanes", J. Tetrahedron Letters, vol. 27, No. 34.
Rathi, et al., pp. 4006–4010, 1989 "Repetitive Imidazole Synthesis . . . ", J. Org. Chem., vol. 55.
Tanaka, et al., pp. 553–559, 1989 "Identification of the Isomeric Hydroxylated Metabolites . . . ", J. Agric. Food Chem., vol. 38.
Vogel, pp. 924–925, 1978, Textbook of Practical Organic Chemistry.

*Primary Examiner*—Richard L. Raymond
*Assistant Examiner*—Brian Bembenick
*Attorney, Agent, or Firm*—Clark R. Carpenter; Joseph F. Leightner

[57] ABSTRACT

Insecticidal compounds having the formula N-(2-$R^a$-3-$R^b$-benzoyl)-N'-(2-$R^c$-3-$R^d$-4-$R^e$-5-$R^f$-benzoyl)-N'-$R^g$-hydrazine, where $R^a$ is a halogen or a lower alkyl; $R^b$ is lower alkoxy; $R^{c-f}$ are selected from hydrogen, bromo, chloro, fluoro, lower alkyl and lower alkoxy; and Rg is a ($C_4$-$C_6$)alkyl or ($C_4$-$C_6$)alkenyl; as well as compositions comprising an agronomically acceptable carrier and an insecticidally effective amount of such compounds; and methods of using such compounds and compositions.

Also, methods for the production of the compounds and their intermediates, which methods comprise admixing a 3-amino-2-(substituted)-benzoic acid, sodium nitrite and methanol under acidic conditions.

2 Claims, No Drawings

INSECTICIDAL N'-SUBSTITUTED-N,N'-DIACYLHYDRAZINES

BACKGROUND OF THE INVENTION

This invention relates to N'-substituted-N,N'-diacylhydrazines which are useful as insecticides, compositions containing those compounds and methods of their use. This invention also relates to the production of intermediates useful in the production of such compounds.

The search for compounds which have a combination of excellent insecticidal activity and low undesirable toxicity is a continuing one because of factors such as the desire for compounds exhibiting greater activity, better selectivity, lower undesirable environmental impact, lower production and market cost and higher effectiveness against insects which are or become resistant to many known insecticides.

Prior processes for the production of the 3-alkoxy-2-alkylbenzoic acid intermediates useful in the production of N'-substituted-N,N'-diacyl-hydrazines of the present invention have the production of 3-hydroxy-2-alkylbenzoic acid compounds from hydrochloride salt of 2-alkyl-3-amino-benzoic acid as a preceding step. Such exothermic anilinium hydrochloride salt reactions pose reaction safety and substance stability concerns and requires controlled cooling. Such constraints can create safety and costs burdens on the production of the useful intermediates concerned herein.

There continues to be a need to develop insecticidal compounds having improved insecticidal and methods of production properties as described above. There also continues to be a need to develop safened processes for the production of the intermediate compounds useful in such methods. The present invention provides improved N'-substituted-N,N'-diacyl-hydrazines which are unexpectedly propertied with enhanced, higher activity as well as a safened method for production of intermediates useful for their production. The combination of higher activity, better economics of manufacture, and safer production methods can provide an economic and environmental advantage in the use of the inventive compounds.

SUMMARY OF THE INVENTION

In accordance with the present invention, there are provided insecticidal compounds having the formula N-(2-Ra-3-Rb-benzoyl)-N'-(2-Rc-3-Rd-4-Re-5-Rf-benzoyl)-N'-Rg-hydrazine, which can be depicted structurally as follows:

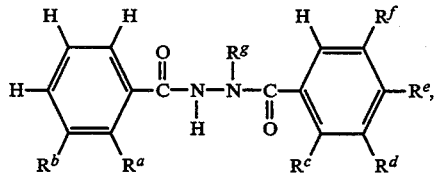

where $R^a$ is a halogen or a lower alkyl; $R^b$ is lower alkoxy, optionally substituted with a halogen (preferably fluorine); Rc-f are independently selected from hydrogen, bromo, chloro, fluoro, lower alkyl and lower alkoxy; and Rg is a $(C_4-C_6)$alkyl or $(C_4-C_6)$alkenyl.

Also provided are compositions comprising an agronomically acceptable carrier and an insecticidally effective amount of such compounds; and methods of using such compounds and compositions.

Also described are improved methods for safer and more direct production of the compounds and their intermediates, which methods comprise effectively admixing a 3-amino-2-(substituted)-benzoic acid, sodium nitrite and methanol under acidic conditions to produce a reaction mass predominantly comprising 3-methoxy-2-(substituted)-benzoic acid.

DETAILED DESCRIPTION OF THE INVENTION

One embodiment of the present invention is an insecticidal compound having a formula of N-(2-$R^a$-3-$R^b$-benzoyl)-N'-(2-$R^c$-3-$R^d$-4-$R^e$-5-$R^f$-benzoyl)-N'-$R^g$-hydrazine, wherein $R^a$ is halogen, preferably bromo or chloro, or a lower alkyl, preferably a $(C_1-C_3)$ alkyl, more preferably methyl; $R^b$ is a lower alkoxy, preferably a $(C_1-C_3)$alkoxy, more preferably methoxy, trifluoromethoxy or ethoxy, most preferably methoxy or ethoxy; $R^c, R^d, R^e$, and $R^f$ are each independently selected from hydrogen, bromo, chloro, fluoro, lower alkyl (preferably a $(C_1-C_3)$alkyl, more preferably methyl) and lower alkoxy (preferably a $(C_1-C_3)$alkoxy, more preferably methoxy); and $R^g$ is a $(C_4-C_6)$alkyl (preferably tert-butyl or neo-pentyl, more preferably tert-butyl) or a $(C_4-C_6)$alkenyl. Either the substituents $R^c$ and $R^d$, or the substituents $R^d$ and $R^e$, or the substituents $R^e$ and $R^f$ can be fused as an ethylenedioxy [—OCH$_2$CH$_2$O—] or propylenedioxy [—OCH$_2$CH$_2$CH$_2$O—] linking group. Structural representation of the embodied compounds can be made as follows:

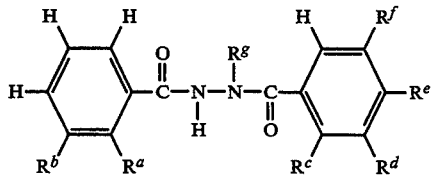

Preferred insecticidal compounds are those wherein $R^b$ is methoxy and Rg is tert-butyl. More preferred are those wherein $R^a$ is methyl, $R^b$ is methoxy, $R^g$ is tertbutyl, and wherein no more than three of $R^c$, $R^d$, $R^e$, and $R^f$ are the same member selected from a group consisting of bromo, chloro, and fluoro or no more than two of $R^d$, $R^e$, and $R^f$ are methoxy. The more preferred compounds are those wherein no more than three of $R^d$, $R^e$, and $R^f$ are independently selected from chloro, methyl and methoxy and the other substituents are hydrogen, and most preferably $R^d$ and $R^f$ are independently selected from chloro, methyl and methoxy and the others are hydrogen.

Preferred compounds because of their higher activity and better economics of production are:

N-(3-methoxy-2-methylbenzoyl)-N'-(3-chloro-5-methylbenzoyl)-N'-tertbutylhydrazine;

N-(3-methoxy-2-methylbenzoyl)-N'-(3,5-dimethylbenzoyl)-N'-tertbutylhydrazine;

N-(3-methoxy-2-methylbenzoyl)-N'-(3,5-dichlorobenzoyl)-N'-tertbutylhydrazine;

N-(3-methoxy-2-methylbenzoyl)-N'-(2,4-dichlorobenzoyl)-N'-tertbutylhydrazine;

N-(3-methoxy-2-methylbenzoyl)-N'-(3-methylbenzoyl)-N'-tertbutylhydrazine;

N-(3-methoxy-2-methylbenzoyl)-N'-benzoyl-N'-tertbutylhydrazine;

N-(3-methoxy-2-methylbenzoyl)-N'-(4-chlorobenzoyl)-N'-tert-butylhydrazine; and
N-(3-methoxy-2-methylbenzoyl)-N'-(3,4,5-trichlorobenzoyl)-N'-tertbutylhydrazine.

Preferred insecticidal compounds wherein Rg is a $(C_5-C_6)$alkyl are those wherein $R^g$ is unsubstituted or substituted neo-pentyl, preferably unsubstituted neo-pentyl or methyl-neo-pentyl. Preferred neo-pentyl compounds are N-(3-methoxy-2-methylbenzoyl)-N'-(3,5-dimethylbenzoyl)-N'-neo-pentyl-hydrazine and N-(3-methoxy-2-methylbenzoyl)-N'-(3,5-dimethylbenzoyl)-N'-methyl-neo-pentylhydrazine.

METHODS OF PREPARATION

Many of the compounds of the present invention, and the intermediates related thereto, can be prepared by methods similar to the known methods for making N'-substituted-N,N'-diacylhydrazines. Those of ordinary skill in the art will be able to utilize or modify such processes after knowledge of the disclosures herein to accommodate many of the functionalities $R^{c-f}$ in the intermediates and compounds of the present invention.

An inventive method to produce some of the intermediates desirable to produce the $R^a$ and $R^b$ functionalities of the present invention has been discovered. This method provides unexpected results in the products and safety of the reaction involved as well as provides a simplified, economic process. The method can be performed by a process comprising effectively admixing a 3-amino-2-(substituted)benzoic acid, sodium nitrite and methanol or a mixture of water and methanol, preferably only methanol, under acidic conditions to produce a reaction mass comprising 3-methoxy-2-(substituted)-benzoic acid.

Accordingly, one embodiment of the present invention is a process comprising admixing
(a) a composition comprising
  (i) a 3-amino-2-(substituted)-benzoic acid or its respective ester and
  (ii) methanol or a mixture of methanol and water; and
(b) an effective amount of an inorganic acid; and
(c) sodium nitrite.

The general reaction scheme can be depicted as follows:

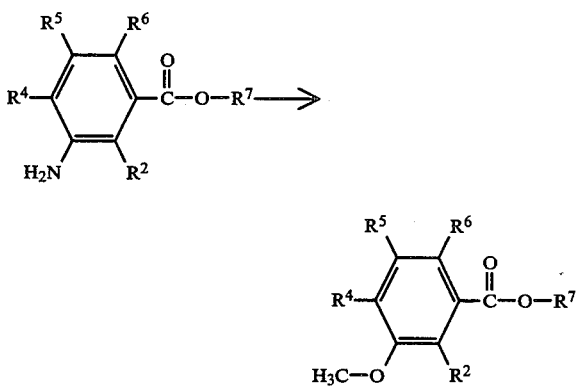

Each of $R^2$, $R^4$, $R^5$, and $R^6$ independently can be hydrogen, a straight or branched $(C_1-C_{10})$alkyl, a straight or branched halo$(C_1-C_{10})$alkyl, a straight or branched $(C_1-C_{10})$alkoxy, a straight or branched halo$(C_1-C_{10})$alkoxy, or a halogen. Preferably $R^2$ is a substituent consistent with the desired compound substitution. A preferred 3-amino-2-(substituted)-benzoic acid is 3-amino-2-methylbenzoic acid. Preferred halogens are bromine, chlorine, and fluorine. A preferred halo($C_1-C_{10}$)alkyl is trifluoromethyl.

$R^7$ can be hydrogen, a straight or branched $(C_1-C_{10})$alkyl, or a straight or branched halo$(C_1-C_{10})$alkyl. Non-limiting illustration of a straight or branched $(C_1-C_{10})$alkyl can be normal-butyl as a straight $C_4$ alkyl and secondary-butyl or iso-butyl as a branched $C_4$ alkyl. The halogenated alkyls can be halogenated with one or more of the same or different halogen. Preferably, $R^7$ is a hydrogen or a $(C_1-C_4)$alkyl, more preferably hydrogen. Some replacement of $R^7$ on the product compound can occur, thus creating a product mixture of acids and esters.

The acidic condition can be created by use of hydrobromic, hydrochloric, phosphoric, or sulfuric acid; preferably sulfuric acid. The amount of the acid is that effective amount in combination with the utilized water or methanol to produce the desired alkoxylated product in substantial amounts. The amount of acid can range from about 0.5 to about 5 mole equivalents, preferably from about 1 to about 4 mole equivalents, more preferably from about 1.5 to about 2.5 mole equivalents.

The amount of alkoxylated product produced in the reaction mass is preferably at least about sixty (60) per cent by weight, more preferably at least about eighty (80) per cent.

The reaction mass can comprise additional products consisting of hydroxylated products (e.g., "phenol compounds") which have hydroxyl moieties (OH) at the 3 position (e.g., 3-hydroxy-2-methylbenzoic acid). Preferably, the hydroxylated by-product content of the reaction mass is less than ten (10) per cent by weight, more preferably less than about five (5) per cent by weight, and most preferably essentially an absence of the hydroxylated by-product.

The reaction mass also can comprise additional products which have replacement moieties bonded to the "ether" oxygen of the carboxylic group of the 3-aminobenzoic acid [e.g., —C(=O)-OH->-C(=O)-OR ], wherein R can be the alkyl portion of the alcohol used, e.g. methyl.

The reaction temperature can be room temperature up to the boiling temperature of the reaction mixture, although cooling can be done but is not required. Preferably the temperature is from about 0° C. to about 100° C., more preferably from about 25° C. to about 75° C., most preferably from about 45° C. to about 65° C.

Since some phenol by-product may be produced by the reaction, an optional method of additional steps to convert any phenol by-product produced in the reaction comprises subsequently admixing the reaction mass formed containing such phenol compounds and
(a) an effective amount of a base, preferably sodium hydroxide, potassium hydroxide, sodium carbonate, or potassium carbonate, more preferably sodium hydroxide and potassium hydroxide, and
(b) an effective amount of a methylating agent, preferably methyl carbonate, methyl chloride, methyl iodide or dimethyl sulfate,
to convert a substantial amount, preferably essentially all, of the phenol compounds to a 3-methoxybenzoic acid or 3-methoxybenzoic ester derivative compound.

The amount of the base used can be preferably about 4 to about 6 equivalents and the amount of the methylating agent used can be preferably about 2 to about 4 equivalents.

Such processes result unexpectedly in a more safe and direct one step route to production of the 3-methoxybenzoic acid relative to prior known processes, which exhibit potential explosion hazards. The enhanced safety is due in part to avoidance of the build-up of diazonium intermediates during the course of the reaction.

The agronomically acceptable salts of the present insecticidal compounds can be synthesized by the utilization of the salting methods known in the art relating to N'-substituted-N,N'-diacylhydrazines used as insecticides.

The compounds of the present invention exhibit unexpectedly excellent results in their use as insecticides. One skilled in the art will be able to determine the activity of a given compound against a given insect and the dosage required to obtain unexpectedly good insecticidal effects. The exact dosage for a given situation can be routinely determined and the compositions and formulations for such uses, and the desired additional components (such as agronomically acceptable carriers, diluents, extenders and other common additives used in insecticidal compositions) can be determined in the known manners.

Accordingly, another embodiment is an insecticidal composition comprising one or more compounds having the formula N-(2-$R^a$-3-$R^b$-benzoyl)-N'-(2-$R^c$-3-$R^d$-4-$R^e$-5-$R^f$-benzoyl)-N'-$R^g$- hydrazine, where $R^a$ is a halogen or a lower alkyl; $R^b$ is lower alkoxy; $R^{c-f}$ are each independently selected from hydrogen, bromo, chloro, fluoro, lower alkyl and lower alkoxy; and Rg is a ($C_4$–$C_6$)alkyl or ($C_4$–$C_6$)alkenyl. The preferred compositions have the preferred compounds set out hereinabove.

Also embodied is a method for controlling insects comprising contacting the insect with an insecticidally effective amount of a compound having the formula N-(2-$R^a$-3-$R^b$-benzoyl)-N'-(2-$R^c$-3-$R^d$-4-$R^e$-5-$R^f$-benzoyl)-N'-$R^g$-hydrazine, wherein $R^a$ is a halogen or a lower alkyl; $R^b$ is lower alkoxy; $R^c$, $R^d$, $R^e$, and $R^f$ are each independently selected from hydrogen, bromo, chloro, fluoro, lower alkyl, and lower alkoxy; and Rg is ($C_4$–$C_6$)alkyl or ($C_4$–$C_6$)alkenyl. The preferred methods will utilize the preferred compounds hereinabove identified. A preferred method is a method wherein $R^a$ is methyl; $R^b$ is methoxy; $R^g$ is tert-butyl; and wherein no more than three of $R^c$, $R^d$, $R^e$, and $R^f$ are the same member selected from a group consisting of bromo, chloro, fluoro, methoxy, and methyl.

The following examples illustrate preparation of the 3-methoxy-2-methylbenzoic acids and the method of preparation of intermediates.

EXAMPLE 1

Preparation of 3-Methoxy-2-Methylbenzoic Acid

3-Amino-2-methylbenzoic acid (140.3 g, 0.93 mol, reacted in four portions) in 5.7 mass equivalents of methanol was treated with 1.5 mole equivalents of concentrated sulfuric acid. The mixture was heated to 55° C. and 1.05 mole equivalent of sodium nitrite dissolved in twice its mass of water was fed to the reaction over 30 to 45 minutes, maintaining the temperature between 55 and 65° C. 4.5 mole equivalents of 25% aqueous sodium hydroxide was added over one-half hour, followed by a half-hour feed of 2 mole equivalents of dimethylsulfate at 50 to 60° C. After one-half hour the batch was assayed by GC. Additional sodium hydroxide and dimethylsulfate were added in portions until complete conversion was obtained. The methanol remaining was removed by vacuum, and the residue was partitioned between ethyl acetate and water made acidic with sulfuric acid. The ethyl acetate was removed under vacuum. The combined residues (152.8 g) dissolved in 350 g warm methanol were poured into a mixture of 278 g concentrated sulfuric acid and 1 liter water. The resulting precipitate was collected by filtration, washed with water, and dried in vacuo, giving 135.8 g (88%) of material which was 96% pure as determined by GC.

EXAMPLE 2

Preparation of 3-Chloro-5-Methylbenzoic Acid

A mixture containing 3,5-dimethylchlorobenzene (25 g, 180 mmol), cobalt (II) acetate tetrahydrate (1.1 g, 4.5 mmol), and sodium bromide (0.46 g, 4.5 mmol) in 50 mL of acetic acid was heated to 85° C. while air was bubbled in. After 55h, the reaction was judged to be complete by GC. After cooling to room temperature, the reaction mixture was filtered. The filtrate was partitioned between water (500 mL) and ethyl acetate (200 mL). The aqueous was extracted with 2×100 mL ethyl acetate. The combined organic phases were washed with water, then extracted with 4% aqueous sodium hydroxide (3×200 mL). The basic aqueous phases were cooled with ice and acidified with concentrated hydrochloric acid. The resulting white precipitate was collected by vacuum filtration and dried to yield 15.5 g of white solid (top 175–177 ° C.) which was consistent with the structure 3-chloro-5-methyl benzoic acid by nmr and GC.

The following examples illustrate the preparation of N-(3-methoxy-2-methylbenzoyl)-N'-(3,5-dimethylbenzoyl)-N'-tert-butylhydrazine.

Step A - 1: Preparation of 3-Amino-2-Methylbenzoic Acid

A solution of 2-methyl-3-nitrobenzoic acid (top. 182–184° C., 22 g, 0.12 mol) in 400 mL of methanol was hydrogenated over platinum oxide (100 rag) for 45 minutes at 55 psi, whereupon the catalyst was filtered off through a bed of Celite® (50 g), and the solvent evaporated under reduced pressure to give 3-amino-2-methylbenzoic acid (top. 178–181° C.) in quantitative yield (18.3 g).

Step A - 2: Preparation of 3-Methoxy-2-Methylbenzoic Acid

Ground 3-amino-2-methylbenzoic acid (17 g, 0.11 mmol) was mixed with methanol (120 mL) in a 1-1 3-neck round bottom flask provided with a mechanical stirrer and a thermometer. To this mixture sulfuric acid (conc., 15.5 mL) was added dropwise with stirring. Upon the addition, the temperature of the mixture went up to 50° C. The addition time was 2 minutes. Following the addition, the flask was placed on a pre-heated oil bath and the temperature of 50–55° C. inside the flask maintained. Thereafter, a dropwise addition of sodium nitrite solution (8.1 g in 17 mL of water) was started. When the temperature reached 62° C., the heating under the oil bath was turned off. After additional 10 rain on the oil bath (the heater still turned off), the temperature dropped to 55° C., at which point sodium hydroxide (50% aqueous, 55 g) diluted water (55 mL) was added dropwise over 30 minutes, followed by water (55 mL) in one portion, and dimethyl sulfate (25 mL) dropwise in two portions (15 plus 10) over 30 minutes with 20 minutes apart. The reaction mixture was allowed to cool to room temperature whereupon it was poured over sulfuric acid (conc., 40 mL) diluted with water (360 mL), the product collected by filtration, and dried in vacuo over 24 hours to give 3-methoxy-2-methylbenzoic acid (12 g, 72%). $^1$H-NMR (CDCl$_3$)δppm 2.50 (s, 3H), 3.85 (s, 3H), 7.03 (d, 1H, Ar), 7.22 (dd, 1H, C-5), 7.59 (d, 1H, Ar).

Step A-3: Preparation of 3-Methoxy-2-Methylbenzoyl Chloride

To 3-methoxy-2-methylbenzoic acid (454 g, 2.73 tool) in 1300 mL chloroform containing 20 g dimethyl formamide at 65° C., thionyl chloride (390 g) was added dropwise over 6 hours, whereupon the solvent was removed by evaporation at a reduced pressure. The residue (512 g) was distilled at 110° C. at 1–2 mm Hg to give 3-methoxy-2-methylbenzoyl chloride (435 g. 85%).

Step B: Preparation of N-(3,5-Dimethylbenzoyl)-N-tert-Butyl-Hydrazine

A suspension of tert-butylhydrazine (290 g, 2.33 mol) in toluene (830 mL) was cooled to 5° C. in an ice bath. Sodium hydroxide (50% aqueous; 180 g, 2.25 mol) mixed with ice (180 g) was slowly added over 30 minutes. To this was added ditertbutyl dicarbonate (500 g; 2.29 tool) over 2 hours, while the temperature of the reaction kept close to 5° C. After the completion, the reaction was allowed to warm to room temperature and stirred overnight. The organic layer was then washed with water and brine, dried over magnesium sulfate, filtered and stripped. The crude product was recrystallized from hexane to give a solid (338.7 g) which melted at 83–86° C. To this solid (320 g, 1.69 tool) in toluene (1 L) at 7° C., 3,5-dimethylbenzoyl chloride (268 g, 1.59 tool) and sodium hydroxide (50% aqueous, 127.23g, 1.59 mol) were added concurrently at such a rate that the temperature of the reaction mixture remained 5–9° C. After addition was complete (2 hours) the reaction mixture was allowed to reach room temperature, whereupon it was diluted with hexane and water, and the product filtered. Additional product was obtained by washing the organic portion of the filtrate with water and brine, evaporation of the solvent followed by trituration with hexane. The combined filtercake (470 g, 1.5 mol, 92% yield) was suspended in methanol (1500 mL) and treated with conc. hydrochloric acid (37%, 357 mL, 3.62 tool) at such a rate that the temperature remained below 35° C. Cooling on ice-bath was applied. After the addition was complete, the reaction mixture was stirred for 72 hours. Additional hydrochloric acid (50 mL) was added and reaction stirred briefly, then neutralized with aqueous sodium bicarbonate. The product was filtered, washed with water and dried to give 256 g, 77.4% yield of N-(3,5-dimethylbenzoyl)-N-tert-butylhydrazine $^1$H-NMR δppm 1.47 (s, 9H, t-Bu) 2.31 (s, 6H), 3.73 (s broad, 2H, NH$_2$) 7,00 (s, 1H, C-4), 7,05 (s, 2H, Ar- C-2 and 6).

Step C: Preparation of N-(3-methoxy-2-methylbenzoyl)-N'-(3,5-dimethylbenzoyl)-N'-tert-butylhydrazine from Products of Step A-2 and Step B A solution of 3-methoxy-2-methylbenzoic acid (1.5 g, 0.01 tool) in thionyl chloride (10 mL) was refluxed for 45 minutes and then stripped under reduced pressure. The residue was dissolved in methylene chloride (50 mL) and added dropwise with cooling at 0° C. to a solution of N-(3,5-dimethylbenzoyl)-N-tertbutylhydrazine (4.4 g. 0.02 mol) in methylene chloride (50 mL). Following the addition, the solution was stirred overnight at room temperature and filtered. The filter-cake was washed extensively with water and ether, and then dried in vacuo to give 2.1 g (64.1% yield) of N-(3-methoxy-2-methylbenzoyl)-N'(3,5-dimethylbenzoyl)-N'-tert-butylhydrazine, melting at 204–204.5° C. $^1$H-NMR δppm 1.50 (s, 9H, tert-Bu), 1.63 (s, 3H, Ar-CH3), 2.25 (s, 6H, di-CH3) 3.75 (s, 6.26 (d, 1H, Ar), 6.93–7.20 (m, 5H, Ar).

Step D - 1: Preparation of N-(3-Methoxy-2-Methylbenzoyl)-N'-tert-Butylhydrazine From Product of Step A-3

To a stirred suspension of tert-butylhydrazine hydrochloride (397 g, 3.27 mol) in methylene chloride (2 L) at 0° C., was added sodium hydroxide (50% aqueous, 260 g) diluted with water (400 mL). Following this, 3-methoxy-2-methylbenzoyl chloride (140 g, 0.78 mol) in methylene chloride (1 L) and sodium hydroxide (50% aqueous, 80 g) diluted with water (400 mL) were added concurrently at −20° C. After the addition was complete, the reaction mixture was allowed to warm to room temperature and after additional 30 minutes, the organic layer was washed with water (4×500 mL), dried over magnesium sulfate and stripped to yield N-(3-methoxy-2-methylbenzoyl)-N'-tert-butylhydrazine (177 g, 96% yield). $^1$H-NMR (CDCl$_3$)δppm 1.19 (s, 9H, t-Bu), 2.29 (s, 3H, CH$_3$), 3.87 (s, 3H, OCH$_3$), 6.90 (d, 1H, C-4 or 6), 6.95 (d, 1H, C-4 or C6) 7.19 (dd, 1H, C-5).

Step D - 2: Preparation of N-(3-Methoxy-2-Methylbenzoyl)-N'-(3,5-Dimethylbenzoyl)-N'-tert-Butylhydrazine From Product of Step D-1

To a stirred solution of N-(3-methoxy-2-methylbenzoyl)-N'-tert-butylhydrazine (506 g, 2.14 mol.) in methylene chloride (1.5 L) at 5° C. were simultaneously added solutions of 3,5-dimethylbenzoyl chloride (360 g, 2.14 mol.) in methylene chloride (500 mL) and sodium hydroxide (50% aqueous, 171.2 g, 2.14 mol) diluted with water (400 mL), at such a rate that the temperature of the mixture did not exceed 10° C. Following the addition, the reaction mixture was allowed to reach room temperature and stirred continuously for 1 additional hour, whereupon the reaction mixture was diluted with methylene chloride (12 L), washed with water, dried over magnesium sulfate, filtered and stripped to give N-(3-methoxy-2-methylbenzoyl)-N'-(3,5-dimethylbenzoyl)-N'-tert-butylhydrazine (663 g, 84.6% yield).

The following table exemplifies, but does not limit, preferred compounds of the present invention. The "SAW - ppm" column headings are the concentration of the Compound at two different concentrations (10 and 2.5 parts per million) and the observed percentage mortality for Southern Army Worm larvae for the concentration.

TABLE 1

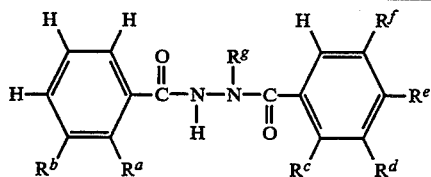

| Comp. No. | Ra | Rb | Rc | Rd | Re | Rf | SAW - ppm 10 | 2.5 |
|---|---|---|---|---|---|---|---|---|
| 1 | CH₃ | OCH₃ | H | CH₃ | H | CH₃ | 100 | 100 |
| 2 | CH₃ | OCH₃ | H | CH₃ | H | H | NT* | 100 |
| 3 | CH₃ | OCH₃ | H | H | H | H | 100 | 100 |
| 4 | CH₃ | OCH₃ | Cl | H | Cl | H | NT | 100 |
| 5 | CH₃ | OCH₃ | Cl | H | H | CH₃ | NT | 100 |
| 6 | CH₃ | OCH₃ | Cl | H | H | H | 100 | 10 |
| 7 | CH₃ | OCH₃ | H | H | F | H | 100 | 100 |
| 8 | CH₃ | OCH₃ | H | H | Cl | H | NT | 100 |
| 9 | CH₃ | OCH₃ | Br | H | H | H | 100 | 0 |
| 10 | CH₃ | OCH₃ | Cl | H | F | H | 100 | 90 |
| 11 | CH₃ | OCH₃ | H | Cl | Cl | H | 100 | 100 |
| 12 | CH₃ | OCH₃ | H | Cl | H | Cl | 100 | 100 |
| 13 | CH₃ | OCH₃ | H | OCH₃ | H | H | 100 | 100 |
| 14 | CH₃ | OCH₃ | F | H | F | H | 100 | 20 |
| 15 | CH₃ | OCH₃ | OCH₃ | H | H | H | 100 | 30 |
| 16 | CH₃ | OCH₃ | H | H | CH₃ | H | 100 | 100 |
| 17 | CH₃ | OCH₃ | H | Cl | H | H | 100 | 100 |
| 18 | CH₃ | OCH₃ | H | CH₃ | CH₃ | H | NT | 100 |
| 19 | CH₃ | OCH₃ | H | F | H | F | 100 | 100 |
| 20 | CH₃ | OCH₃ | H | Br | H | H | 100 | 60 |
| 21 | CH₃ | OCH₃ | H | Cl | H | CH₃ | NT | 100 |
| 22 | CH₃ | OCH₃ | H | OCH₃ | H | CH₃ | NT | 100 |
| 23 | CH₃ | OCH₃ | H | OCH₃ | CH₃ | H | 100 | 100 |
| 24 | CH₃ | OCH₃ | H | CH₃ | Cl | H | 100 | 100 |
| 25 | CH₃ | OCH₃ | OCH₃ | H | Cl | H | 100 | 100 |
| 26 | CH₃ | OCH₃ | H | Br | H | CH₃ | NT | 100 |
| 27 | CH₃ | OCH₃ | H | Br | H | Cl | 100 | 100 |
| 28 | CH₃ | OCH₃ | H | Cl | F | H | 100 | 100 |
| 29 | CH₃ | OCH₃ | H | F | H | H | 100 | 100 |
| 30 | CH₃ | OCH₃ | H | F | F | H | 100 | 100 |
| 31 | CH₃ | OCH₃ | OCH₃ | H | CH₃ | H | NT | 100 |
| 32 | CH₃ | OCH₃ | H | Cl | Cl | Cl | (100% at 0.6 ppm) | |
| 33 | CH₃ | OCH₃ | H | F | F | F | 100 | 100 |
| 34 | CH₃ | OCH₃ | H | OCH₃ | CH₃ | OCH₃ | 100 | 100 |
| 35 | CH₃ | OCH₃ | H | CH₃ | H | CH₃ | 100 | 100 |
| 36 | Br | OCH₃ | H | CH₃ | H | CH₃ | NT | 100 |
| 37 | Cl | OCH₃ | H | CH₃ | H | CH₃ | NT | 100 |
| 38 | CH₃ | OCF₃ | H | CH₃ | H | CH₃ | NT | 100 |
| 39 | CH₃ | OCH₂CH₃ | H | CH₃ | H | CH₃ | NT | 100 |

For all compounds Rg is tert-butyl, except that for compound 35 Rg is neo-pentyl. NT signifies compound not tested at this ppm.

It should be understood that the instant specification and examples are set forth by way of illustration and not limitation, and that various modifications and changes may be made without departing from the spirit and scope of the present invention as defined by the appended claims.

What is claimed is:

1. A process for producing 3-methoxy-2-(substituted)-benzoic acid or ester of 3-methoxy-2-(substituted)-benzoic acid comprising admixing at a temperature of from about 25 degrees Centigrade to about 75 degrees Centigrade
    (a) a con, position comprising
        (i) a 3-amino-2-(substituted)-benzoic acid or its respective ester and
        (ii) methanol or a mixture of methanol and water under acidic conditions; and
    (b) an effective amount of an inorganic acid; and
    (c) sodium nitrite.
2. The process of claim 1 wherein the inorganic acid is selected from hydrobromic acid, hydrochloric acid, phosphoric acid, and sulfuric acid.

* * * * *